(12) United States Patent
Huh

(10) Patent No.: US 8,806,662 B2
(45) Date of Patent: Aug. 19, 2014

(54) WELDING HELMET WITH PROTECTION COVER FOR CARTRIDGE

(75) Inventor: Moon Young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 0 days.

(21) Appl. No.: 12/062,114

(22) Filed: Apr. 3, 2008

(65) Prior Publication Data
US 2009/0000001 A1    Jan. 1, 2009

(30) Foreign Application Priority Data

Jun. 27, 2007   (KR) .......................... 10-2007-0063627

(51) Int. Cl.
*A61F 9/06* (2006.01)

(52) U.S. Cl.
CPC .................................... *A61F 9/067* (2013.01)
USPC ........................................... 2/8.7; 2/8.2; 2/8.4

(58) Field of Classification Search
USPC ........ 2/410, 7, 8.1, 8.2, 8.3, 8.4, 8.5, 8.6, 8.7, 2/8.8, 431, 432, 10, 422, 424, 427, 905, 2/906; D29/110
See application file for complete search history.

(56) References Cited

U.S. PATENT DOCUMENTS

| | | | |
|---|---|---|---|
| 4,853,973 A * | 8/1989 | Boochard ............................ 2/8.1 |
| 4,863,244 A * | 9/1989 | Fuerthbauer et al. ............ 349/14 |
| 5,302,815 A * | 4/1994 | Eggenschwiler .......... 250/201.1 |
| D349,588 S * | 8/1994 | Howard et al. .............. D29/110 |
| 5,533,206 A | 7/1996 | Petrie et al. |
| D393,933 S | 4/1998 | Huh |
| 5,959,705 A * | 9/1999 | Fergason ......................... 349/14 |
| 6,021,520 A * | 2/2000 | Wang-Lee ........................... 2/8.8 |
| 6,067,129 A * | 5/2000 | Fergason ......................... 349/14 |
| 6,070,264 A | 6/2000 | Hamilton et al. |
| 6,151,711 A * | 11/2000 | Edwards ............................ 2/8.3 |
| 6,185,739 B1 * | 2/2001 | Verkic et al. ....................... 2/8.1 |
| D446,887 S | 8/2001 | Young |
| 6,401,244 B1 * | 6/2002 | Kramer et al. ..................... 2/8.1 |
| 6,557,174 B2 * | 5/2003 | Martin et al. ...................... 2/8.8 |
| 6,614,409 B1 * | 9/2003 | Bae .................................... 345/8 |
| D481,832 S | 11/2003 | Huh |
| D482,502 S | 11/2003 | Huh |
| D482,503 S | 11/2003 | Huh |
| D489,492 S * | 5/2004 | Wu .............................. D29/110 |
| 6,891,681 B2 * | 5/2005 | Schindele ..................... 359/707 |
| 6,934,967 B2 * | 8/2005 | Miyashita et al. ................. 2/8.8 |
| 6,973,672 B2 * | 12/2005 | Huh ................................... 2/8.1 |
| D521,190 S * | 5/2006 | Wu .............................. D29/110 |
| 7,161,116 B2 * | 1/2007 | Steinemann .................. 219/147 |
| 7,284,281 B2 | 10/2007 | Huh |
| 7,308,719 B2 | 12/2007 | Huh |
| D565,801 S * | 4/2008 | Curci et al. ................. D29/110 |
| 2003/0033661 A1 | 2/2003 | Huh |

(Continued)

*Primary Examiner* — Khoa Huynh
*Assistant Examiner* — Andrew W Collins
(74) *Attorney, Agent, or Firm* — Cantor Colburn LLP

(57) ABSTRACT

Disclosed is a welding helmet with a protection cover for a cartridge, being manufactured in various forms and capable of covering a cartridge of the welding helmet and thereby protecting the cartridge from welding heat and preventing melting of the cartridge. According to the present invention, the welding helmet comprising a helmet body covering an operator's face, an opening formed on a front of the helmet body, and a cartridge connected with the opening and equipped with an LCD panel which intercepts light emanating from a welding operation to protect the operator's eyes, further comprises a heat transmission interception unit formed on a front of the cartridge of the welding helmet to prevent surface deformation caused by welding heat.

3 Claims, 4 Drawing Sheets

(56) References Cited

U.S. PATENT DOCUMENTS

| | | | |
|---|---|---|---|
| 2004/0210976 A1* | 10/2004 | Huh | 2/8 |
| 2006/0080761 A1 | 4/2006 | Huh | |
| 2006/0153997 A1* | 7/2006 | Rankin et al. | 428/1.5 |
| 2006/0185052 A1* | 8/2006 | Huh | 2/8.2 |
| 2007/0079417 A1* | 4/2007 | Huh | 2/8.2 |
| 2007/0080621 A1 | 4/2007 | Huh | |
| 2007/0220649 A1 | 9/2007 | Huh | |
| 2008/0060102 A1* | 3/2008 | Matthews et al. | 2/8.2 |
| 2008/0092259 A1* | 4/2008 | Seo | 2/12 |
| 2008/0120752 A1 | 5/2008 | Huh | |
| 2013/0097760 A1* | 4/2013 | Feinberg | 2/8.2 |

* cited by examiner

Fig. 1  *Prior Art*

WELDING HELMET WITH PROTECTION COVER FOR CARTRIDGE

BACKGROUND OF THE INVENTION

1. Field of the Invention

The present invention relates to a welding helmet with a protection cover for a cartridge, and more particularly to a welding helmet equipped with a protection cover, being manufactured in various forms, capable of covering a cartridge of the welding helmet and thereby protecting the cartridge from sparks flying about during a welding operation and preventing melting of the cartridge.

2. Description of the Related Art

In general, a welding helmet protects an operator's eyes and face while the operator is performing welding or cutting. Such a welding helmet is equipped with an anti-dazzling device (hereinafter, referred to as a 'cartridge') to protect the operator's eyes from harmful intense light rays generated during the welding or cutting. Generally, the cartridge intercepts light rays greater than 780 nm (IR) and less than 365 nm (UV) and controls transmission of visible rays so that the operator is able to check a welding position without feeling dazzled.

U.S. Pat. No. 5,533,206 discloses a welding helmet incorporating an EQC (electronic quick change) cartridge and a cartridge housing. The EQC cartridge includes a liquid crystal display (LCD) lens positioned directly in front of the eyes of the wearer, thereby functioning as the actual viewing window, solar cells absorbing light and functioning as the energy input, and photo sensor cells detecting sparks and other intense light and acting as the input to a circuit that automatically adjusts the LCD lens to a variable opaque condition. The cartridge housing is located inside of the helmet to retain the cartridge within the helmet.

U.S. Pat. No. 6,070,264 discloses a welding helmet having a shutter assembly comprising a shutter through which the wearer of the helmet may view a welding operation being performed, the shutter having an associated electronic control for controlling a light transmission shade of the shutter, the control including a light sensor for sensing light emanating from the welding operation, and the control having an electronic circuit for driving the shutter to a darker shade in response to the light sensor sensing brighter light from the welding operation.

Although the conventional welding helmet is equipped with a cartridge which detects intense light emanating from the welding operation and automatically adjusts the LCD lens and the shutter to a darker shade so as to protect the operator's eyes, there remains a shortcoming in that installation and removal of the cartridge with respect to the welding helmet is so cumbersome. The cartridge mounted to the welding helmet needs to be conveniently installed and removed in order to prepare for when repair or replacement of parts is required. However, the EQC cartridge and a cartridge in the form of the shutter assembly of the conventional welding helmets are irremovable or difficult to remove. Furthermore, in the conventional welding helmet having a removable cartridge, connection between a helmet body and the cartridge is not achieved tightly enough to prevent fumes generated from the welding or cutting operation from flowing in through the gap between the helmet body and the cartridge. The fumes directly flowing in the welding helmet can seriously affect the operator's health.

In addition, the conventional welding helmets are subject to heat generated from the welding operation. Therefore, the welding helmets may be melted by heat or damaged especially at delicate portions where electronic parts are built in.

SUMMARY OF THE INVENTION

Therefore, the present invention has been made in view of the above problems, and it is an object of the present invention to provide a welding helmet with a protection cover for a cartridge, being manufactured in various forms, capable of covering the cartridge and thereby preventing the cartridge from being melted by welding heat generated from a welding operation.

In accordance with the present invention, the above and other objects can be accomplished by the provision of a welding helmet with a protection cover for a cartridge, comprising a helmet body covering an operator's face, an opening formed on a front of the helmet body, and a cartridge connected with the opening to intercept light emanating from a welding operation to protect the operator's eyes, the welding helmet further comprising the protection cover at an upper surface of the cartridge.

According to the embodiment of the present invention, the protection cover of the welding helmet is implemented by any one selected from a group consisting of a lower cover covering a lower part of the LCD panel, a front cover including a panel opening for the LCD panel at a lower part thereof and a cell opening for a rechargeable solar cell at an upper part thereof, a lower coating cover covering the lower part of the LCD panel, and a front coating cover including a panel opening for the LCD panel at a lower part thereof and a cell opening for a rechargeable solar cell at an upper part thereof.

The protection cover may be made of any one material among silver foil, a heat resistant resin plate, a heat resistant film, a heat resistant coating layer, and a heat resistant metal plate. In addition, according to the embodiments of the present invention, the protection is removably connected to the welding helmet.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE PREFERRED EMBODIMENTS

Hereinafter, a welding helmet with a protection cover for a cartridge according to an exemplary embodiment of the present invention will be described in detail with reference to the accompanying drawings.

Figure 1:
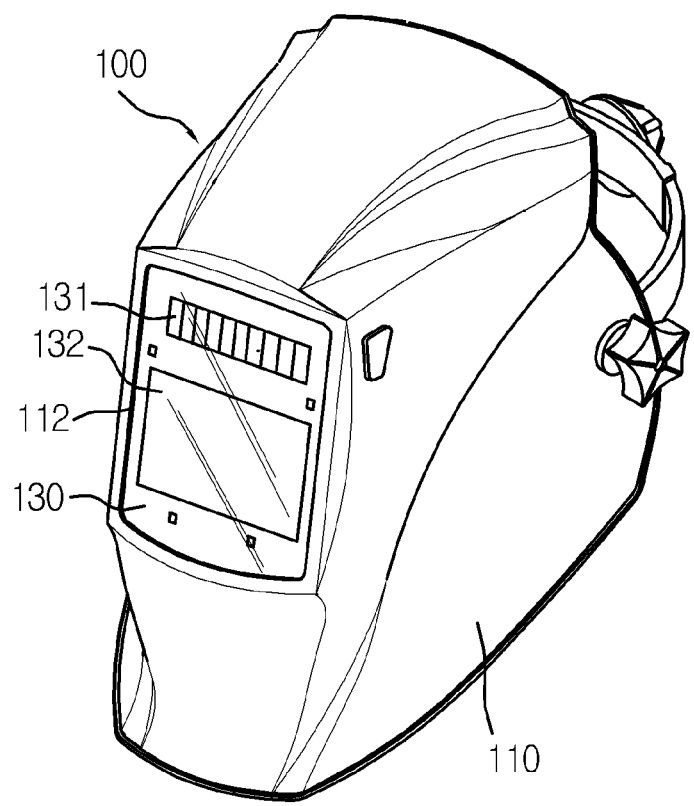
FIG. 1 is a perspective view of a conventional welding helmet.

FIG. 1 a perspective view of a conventional welding helmet. As shown in FIG. 1, the welding helmet 100 comprises a helmet body 110 covering an operator's face, an opening 112 formed on a front of the helmet body 110, and a cartridge 130 connected to the opening 112 to intercept light emanating from a welding operation and thereby protect the operator's eyes from the light. The helmet body 110 is made of a light material such as incombustible plastic and structured to include the opening 112 of a square form on the front thereof. The cartridge 130 is removably mounted to the opening 112. In addition, connecting/removing units are provided around the inside of the opening 112 and at corresponding positions of the helmet body 110 for connection and removal of the cartridge 130 with respect to the helmet body 110.

FIGS. 2 to 6 show a welding helmet equipped with a protection cover according to embodiments of the present invention. Referring to FIGS. 2 to 6, the welding helmet 100 comprising the helmet body 110 covering the operator's face, the opening 112 formed on the front of the helmet body 110, and the cartridge 130 connected to the opening 112 to intercept light emanating from the welding operation and thereby protect the operator's eyes from the light, is further equipped with a protection cover disposed at the front of the cartridge 130 to prevent thermal deformation of a surface of the cartridge 130.

Figure 2:
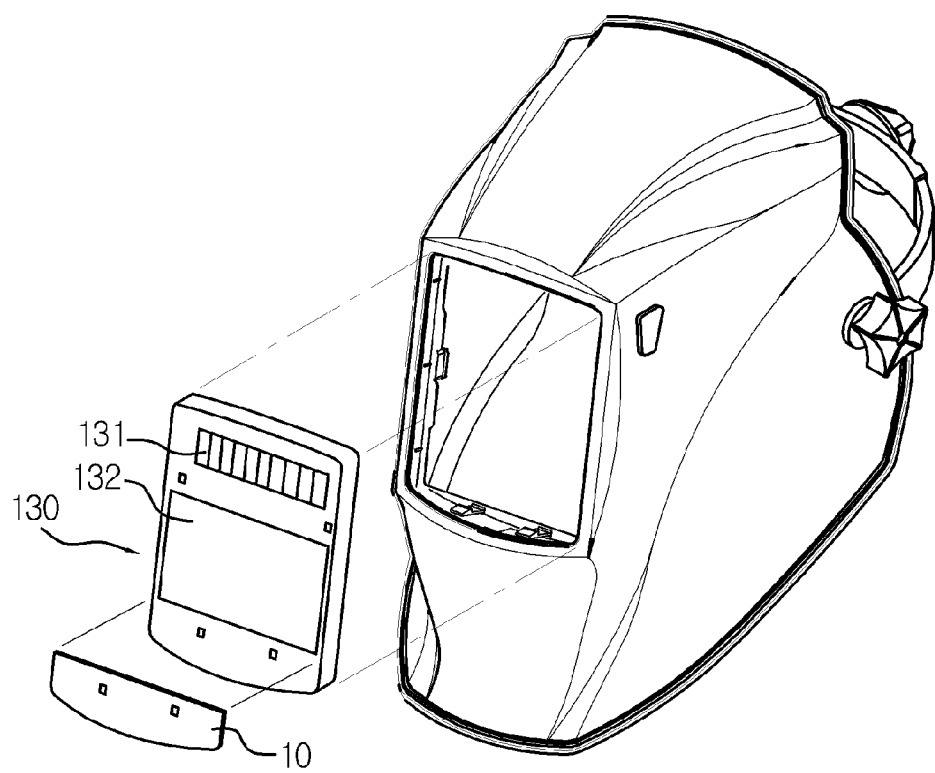
FIG. 2 is a perspective view of a welding helmet equipped with a protection cover according to an embodiment of the present invention.
Figure 3:
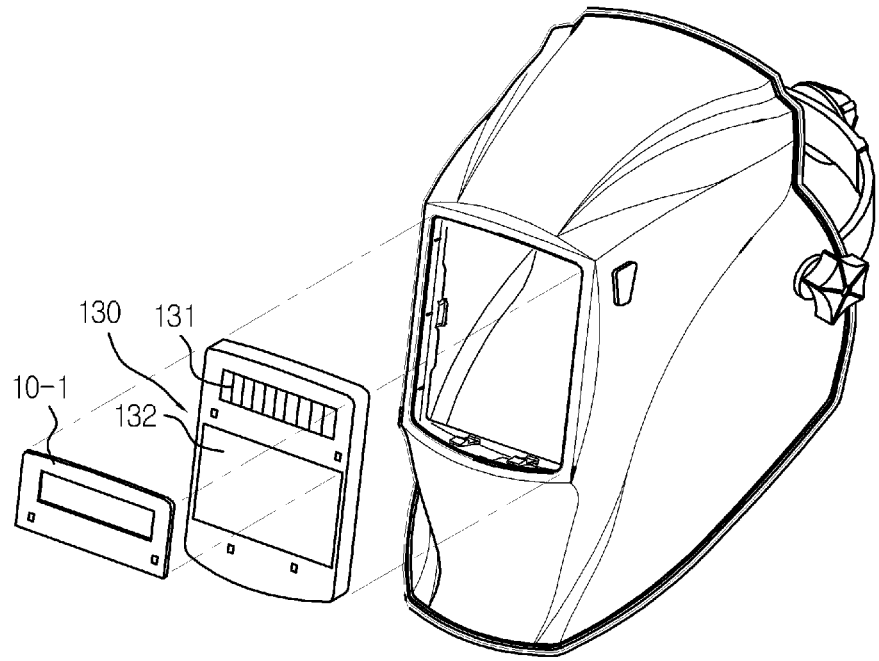
FIG. 3 is an exploded perspective view of a welding helmet equipped with a protection cover according to another embodiment of the present invention.
Figure 4:
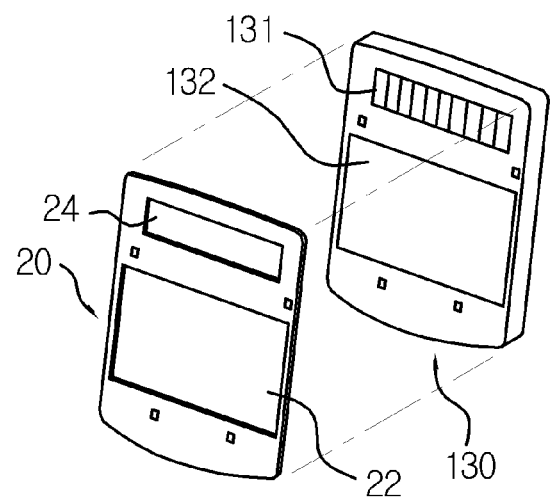
FIG. 4 shows a state where a protection cover according to yet another embodiment of the present invention is mounted to the welding helmet.

The protection cover mounted to the front of the cartridge 130 can be manufactured in various configurations. For example, the protection cover may include a lower cover 10, which covers a portion below an LCD panel 132 of the cartridge 130, or an upper cover 10-1 which covers a portion above the LCD panel 132 of the cartridge 130, as shown in FIGS. 2 and 3 respectively, thereby preventing the cartridge 130 from melting by welding heat. Referring to FIG. 4, the protection cover may include a front cover 20. The front cover 20 includes a panel opening 22 for exposing the LCD panel 132 of the cartridge 130, and a cell opening 24 for exposing a rechargeable solar cell 131 of the cartridge 130. The above-structured front cover 20 is capable of protecting the cartridge 130 from the welding heat, by covering the cartridge 130 except for the LCD panel 132 and the rechargeable solar cell 131 of the cartridge 130, as shown in FIG. 4. Also, thermal deformation of the cartridge 130 can be prevented.

Figure 5:
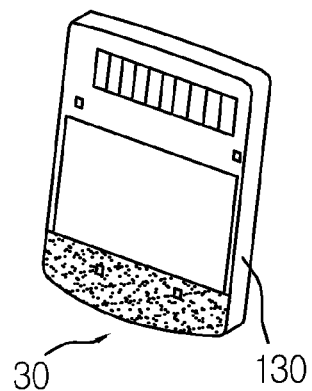
FIG. 5 shows a state where a protection cover according to yet another embodiment of the present invention is mounted to the welding helmet.
Figure 6:
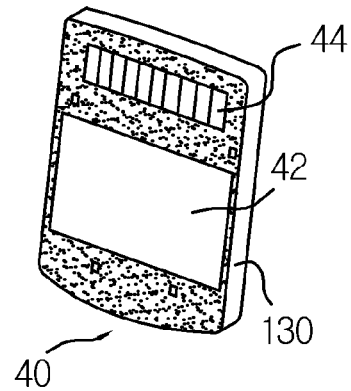
FIG. 6 shows a state where a protection cover according to still yet another embodiment of the present invention is mounted to the welding helmet.

The protection cover according to the embodiment of the present invention may be manufactured in various types of coating layers. For example, when a lower coating cover 30 covering the lower part of the LCD panel 132 of the cartridge 130 is used as shown in FIG. 5, the cartridge 130 can be protected from sparks of the welding operation not to be melted by the sparks. In addition, as shown in FIG. 6, a front coating cover 40 comprising a panel opening 42 of the LCD panel 132 at a lower part thereof and a cell opening 44 of a rechargeable solar cell 131 at an upper part thereof may be used to prevent the cartridge 130 from being melted by the welding sparks, by covering the lower part of the LCD panel 132 of the cartridge 130.

The protection cover of the welding helmet according to the embodiments of the present invention may be made of any one material among silver foil, a heat resistant resin plate, a heat resistant film, a heat resistant coating layer and a heat resistant metal plate. Also, the protection cover is configured to be removable so as to be freely connected and removed as necessary.

The protection cover which is applied to the cartridge 130 according to the embodiments of the present invention is formed by vacuum-deposition coating a partial or the whole surface of the LCD panel 132.

As apparent from the above description, the present invention provides a welding helmet with a protection cover for a cartridge, which is capable of preventing melting of the cartridge during the welding operation, by covering the cartridge according to various configurations thereof. Furthermore, the welding helmet is very useful in the field of a safety equipment industry since it is effective in preventing deformation and functional failure.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A welding helmet comprising:
   a helmet body covering an operator's face, an opening formed on a front of the helmet body;
   a cartridge connected with the opening and equipped with a rechargeable solar cell and an LCD panel to intercept light emanating from a welding operation to protect the operator's eyes; and
   a protection cover formed on a front of the cartridge of the welding helmet to prevent surface deformation caused by welding heat, the protection cover comprising a front cover removably connected to an outer facing surface of the cartridge, the front cover including a first opening for the LCD panel at a lower part thereof and a second opening for a rechargeable solar cell at an upper part thereof.

2. The welding helmet of claim 1, wherein the protection cover is made of any one material among silver foil, a heat resistant resin plate, a heat resistant film, a heat resistant coating layer, and a heat resistant metal plate.

3. The welding helmet of claim 1, wherein the protection cover is formed by vacuum-deposition coating a partial or the whole surface of the LCD panel formed at the cartridge.

* * * * *